(12) United States Patent
Jasienski et al.

(10) Patent No.: US 6,830,922 B2
(45) Date of Patent: Dec. 14, 2004

(54) SYSTEM AND METHOD FOR INOCULATING A BIOLOGICAL REACTOR

(75) Inventors: Raymond Jasienski, Englishtown, NJ (US); Younghua Yang, Plainsboro, NJ (US)

(73) Assignee: Envirogen, Inc., Lawrenceville, NJ (US)

(*) Notice: Subject to any disclaimer, the term of this patent is extended or adjusted under 35 U.S.C. 154(b) by 298 days.

(21) Appl. No.: 10/036,962

(22) Filed: Dec. 21, 2001

(65) Prior Publication Data

US 2003/0119180 A1 Jun. 26, 2003

(51) Int. Cl.⁷ .............................................. C12M 1/00
(52) U.S. Cl. .................... 435/289.1; 435/325; 435/420; 435/260; 435/294.1; 435/309.2; 435/819; 210/610; 210/205; 210/209
(58) Field of Search ................................ 435/325, 420, 435/260, 289.1, 294.1, 307.1, 309.1, 309.2, 813, 819; 210/610, 621, 623, 626, 167, 195.1, 209, 205

(56) References Cited

U.S. PATENT DOCUMENTS

| 4,156,630 A | * | 5/1979 | Muller ........................ 435/261 |
| 4,686,189 A | * | 8/1987 | Redikultsev et al. .... 435/286.5 |
| 5,661,030 A | * | 8/1997 | Roslonski ................ 435/290.2 |
| 5,811,289 A | * | 9/1998 | Lewandowski et al. ..... 435/262 |

* cited by examiner

Primary Examiner—David A. Redding
(74) Attorney, Agent, or Firm—RatnerPrestia (57) ABSTRACT

A system and method are provided for inoculating a biological reactor having a chamber. The chamber is configured to contain influent and biomass to degrade contaminants in the influent. A vessel is configured to receive influent and biomass from the chamber and to substantially isolate the received influent and biomass from that contained in the chamber. The vessel is also configured to deliver the isolated influent and biomass to the chamber, thereby facilitating inoculation of the biological reactor.

39 Claims, 6 Drawing Sheets

SYSTEM AND METHOD FOR INOCULATING A BIOLOGICAL REACTOR

FIELD OF THE INVENTION

This invention relates to a system and method for renewing biological activity in a biological reactor. More specifically, this invention relates to accelerating the renewal of biological activity in a biological reactor in the event of a reduction in the activity of the biomass contained therein.

BACKGROUND OF THE INVENTION

Efforts to protect the environment include advanced biological treatment of wastewater through the use of biological reactors. It is the activity of biomass within the biological reactor that degrades contaminants in the influent to effect a filtration process. At times there may be a reduction in biomass activity which can seriously limit the effectiveness of the biological reactor, and in some extreme cases cease the functioning of the biological reactor altogether. The remedy is to inoculate the biological reactor to renew its biological activity, thereby restoring the efficacy of the biological reactor.

Conventional methods of inoculation in biological reactors can, however, be quite involved, costly, and time consuming. For example, the process may consist of fermenting and thickening an inoculum in a laboratory to suit a particular application, which often takes several weeks. During the time elapsed until the inoculum is prepared, the biological reactor is not operational. This period of downtime can be costly and highly inefficient.

After the inoculum is prepared, it must be transported from the laboratory to the biological reactor. Because the laboratory in which the inoculum is prepared is often remote from the biological reactor, the cost for such transportation is usually significant. This is especially true given that the inoculum is heavy (in slurry form) and significant in volume. Time is also lost during transportation, thereby extending the downtime of the biological reactor.

Once shipped or otherwise transported to the field location, the lab-developed inoculum may then need time to acclimate to actual field conditions. While efforts are made to simulate the conditions of the biological reactor at the laboratory, the inoculum will often need time to adjust to the actual biological reactor and the conditions under which it operates. This acclimation period also extends the downtime or recovery time of the biological reactor.

The distinct requirements for producing inoculum for each application in a laboratory setting, combined with the field labor necessary to handle the shipment and introduce the inoculum to the biological reactor, make this conventional inoculation method a rather costly enterprise.

Accordingly, there is a need for an improved system and method for inoculating a biological reactor.

SUMMARY OF THE INVENTION

This invention provides a system for inoculating a biological reactor having a chamber. The chamber is configured to contain influent and biomass to degrade contaminants in the influent. A vessel is configured to receive influent and biomass from the chamber and to substantially isolate the received influent and biomass from that contained in the chamber. The vessel is also configured to deliver the isolated influent and biomass to the chamber, thereby facilitating inoculation of the biological reactor.

This invention also provides a system for inoculating a biological reactor having a chamber configured to contain influent and biomass to degrade contaminants in the influent, wherein the system includes means for substantially isolating influent and biomass received from the chamber from influent and biomass contained in the chamber. The system also includes means for delivering isolated influent and biomass to the chamber, thereby facilitating inoculation of the biological reactor.

Additionally, this invention provides a method for inoculating a biological reactor having a chamber adapted to contain influent and biomass to degrade contaminants in the influent. A portion of influent and biomass received from the chamber is substantially isolated from influent and biomass in the chamber. At least a portion of the isolated influent and biomass is delivered to the chamber, thereby inoculating the biological reactor.

Moreover, this invention provides a method for configuring a biological reactor for inoculation, wherein the biological reactor includes a chamber adapted to contain influent and biomass to degrade contaminants in the influent. A vessel is connected to receive influent and biomass from the chamber, wherein the vessel is configured to substantially isolate received influent and biomass from that in the chamber. At least a portion of the isolated influent and biomass is returned from the vessel to the chamber.

This invention also provides a biological reactor including a chamber configured to contain influent and biomass to degrade contaminants in the influent, and a vessel configured to substantially isolate influent and biomass from that contained in the chamber. The vessel is configured to receive influent and biomass from the chamber. The vessel is also configured to deliver isolated influent and biomass to the chamber, thereby facilitating inoculation of the biological reactor.

Furthermore, this invention provides a method for providing inoculum for a biological reactor having a chamber adapted to contain influent and biomass to degrade contaminants in the influent. A portion of influent and biomass received from the chamber is substantially isolated from influent and biomass in the chamber. The isolated influent and biomass is maintained at substantially the same temperature as in the chamber.

BRIEF DESCRIPTION OF THE DRAWINGS

The invention will be described with reference to the exemplary embodiments illustrated in the figures of which.

DETAILED DESCRIPTION OF THE INVENTION

Preferred features of embodiments of this invention will now be described with reference to the figures. It will be appreciated that the spirit and scope of the invention is not limited to the embodiments selected for illustration. Also, it should be noted that the drawings are not rendered to any particular scale or proportion. It is contemplated that any of the configurations and materials described hereafter can be modified within the scope of this invention.

When there is a reduction in biomass activity in a biological reactor, the biological reactor is preferably inoculated to renew its biological activity to restore the functioning of the biological reactor. The current method of biomass inoculation in biological reactors can be quite involved, costly, and time consuming. Accordingly, this invention provides an improved system and method for renewing biological activity in a biological reactor.

Generally, with reference to FIGS. 1 through 6, this invention provides a system for inoculating a biological reactor having a chamber 2. The chamber 2 is configured to contain influent 4 and biomass 6 to degrade contaminants in the influent 4. A vessel 8 is configured to receive influent 4 and biomass 6 from the chamber 2 and to substantially isolate the received influent 4 and biomass 6 from that contained in the chamber 2. The vessel 8 is also configured to deliver the isolated influent 4 and biomass 6 to the chamber 2, thereby facilitating inoculation of the biological reactor.

This invention also provides a system for inoculating a biological reactor having a chamber 2 configured to contain influent 4 and biomass 6 to degrade contaminants in the influent 4, wherein the system includes a means for substantially isolating influent 4 and biomass 6 received from the chamber 2 from influent 4 and biomass 6 contained in the chamber 2. The system also includes a means for delivering isolated influent 4 and biomass 6 to the chamber 2, thereby facilitating inoculation of the biological reactor.

Additionally, this invention provides a method for inoculating a biological reactor having a chamber 2 adapted to contain influent 4 and biomass 6 to degrade contaminants in the influent 4. A portion of influent 4 and biomass 6 received from the chamber 2 is substantially isolated from influent 4 and biomass 6 in the chamber 2. At least a portion of the isolated influent 4 and biomass 6 is delivered to the chamber 2, thereby inoculating the biological reactor.

Moreover, this invention provides a method for configuring a biological reactor for inoculation, wherein the biological reactor includes a chamber 2 adapted to contain influent 4 and biomass 6 to degrade contaminants in the influent 4. A vessel 8 is connected to receive influent 4 and biomass 6 from the chamber 2. The vessel 8 is configured to substantially isolate received influent 4 and biomass 6 from that in the chamber 2. At least a portion of the isolated influent 4 and biomass 6 is returned from the vessel 8 to the chamber 2.

This invention also provides a biological reactor including a chamber 2 configured to contain influent 4 and biomass 6 to degrade contaminants in the influent 4, and a vessel 8 configured to substantially isolate influent 4 and biomass 6 from that contained in the chamber 2. The vessel 8 is configured to receive influent 4 and biomass 6 from the chamber 2. The vessel 8 is also configured to deliver isolated influent 4 and biomass 6 to the chamber 2, thereby facilitating inoculation of the biological reactor.

Furthermore, this invention provides a method for providing inoculum for a biological reactor having a chamber 2 adapted to contain influent 4 and biomass 6 to degrade contaminants in the influent 4. A portion of influent 4 and biomass 6 received from the chamber 2 is substantially isolated from influent 4 and biomass 6 in the chamber 2. The isolated influent 4 and biomass 6 is maintained at substantially the same temperature as in the chamber 2.

Figure 1:
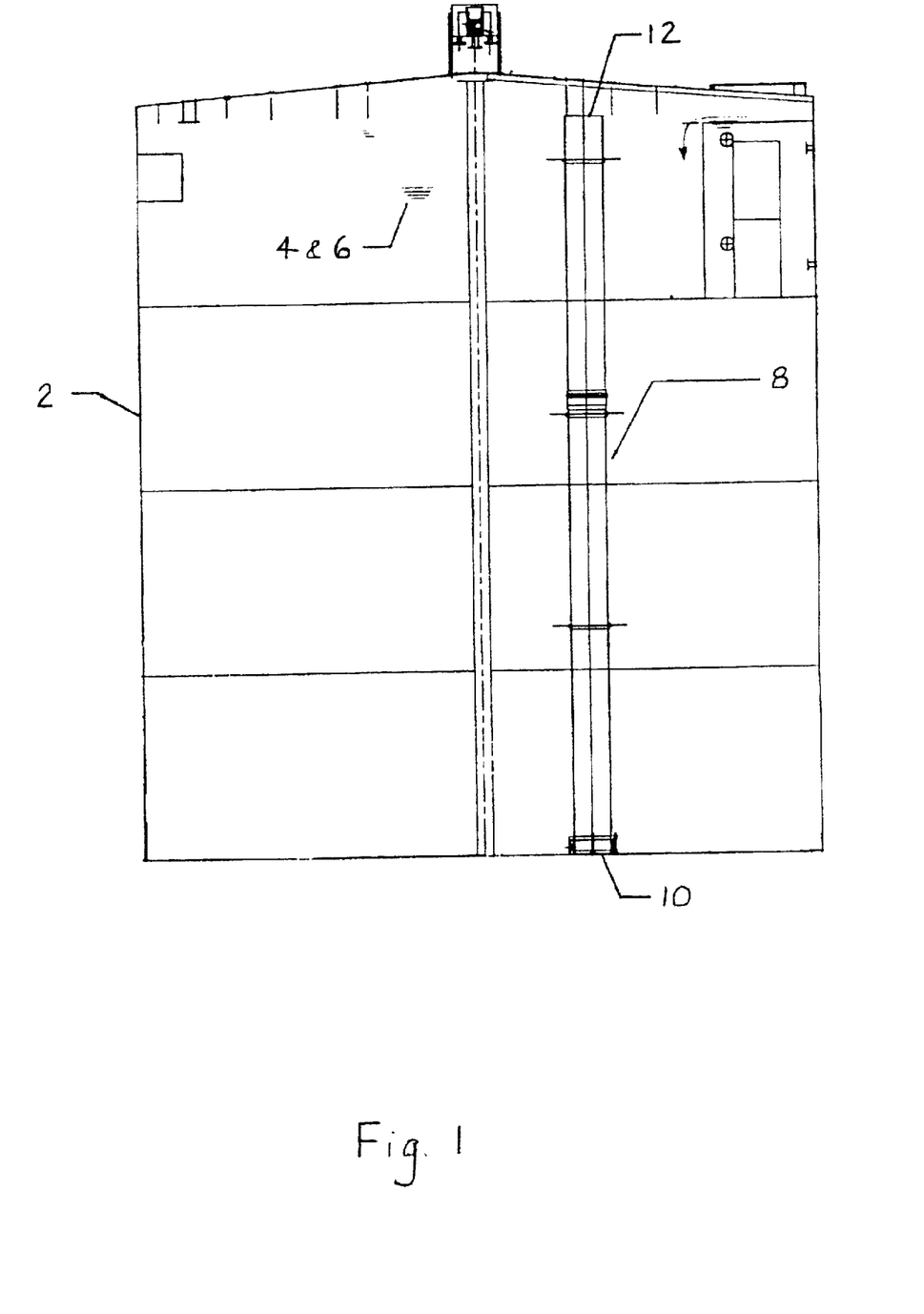
FIG. 1 is a side view of an embodiment of a biological reactor according to this invention.

One embodiment of a system according to this invention is illustrated in FIG. 1. A chamber 2, typically constructed of a metallic material such as coated carbon steel, serves as an enclosure to contain influent 4 and biomass 6 to degrade contaminants in the influent 4. A vessel 8, typically constructed of a plastic material such as polyvinyl chloride, is positioned within the chamber 2. A bottom end 10 of the vessel 8 is secured to the bottom surface of the chamber 2, and an open top 12 of the vessel 8 extends above the level of the influent 4 and biomass 6 contained in the chamber 2.

Figure 2:
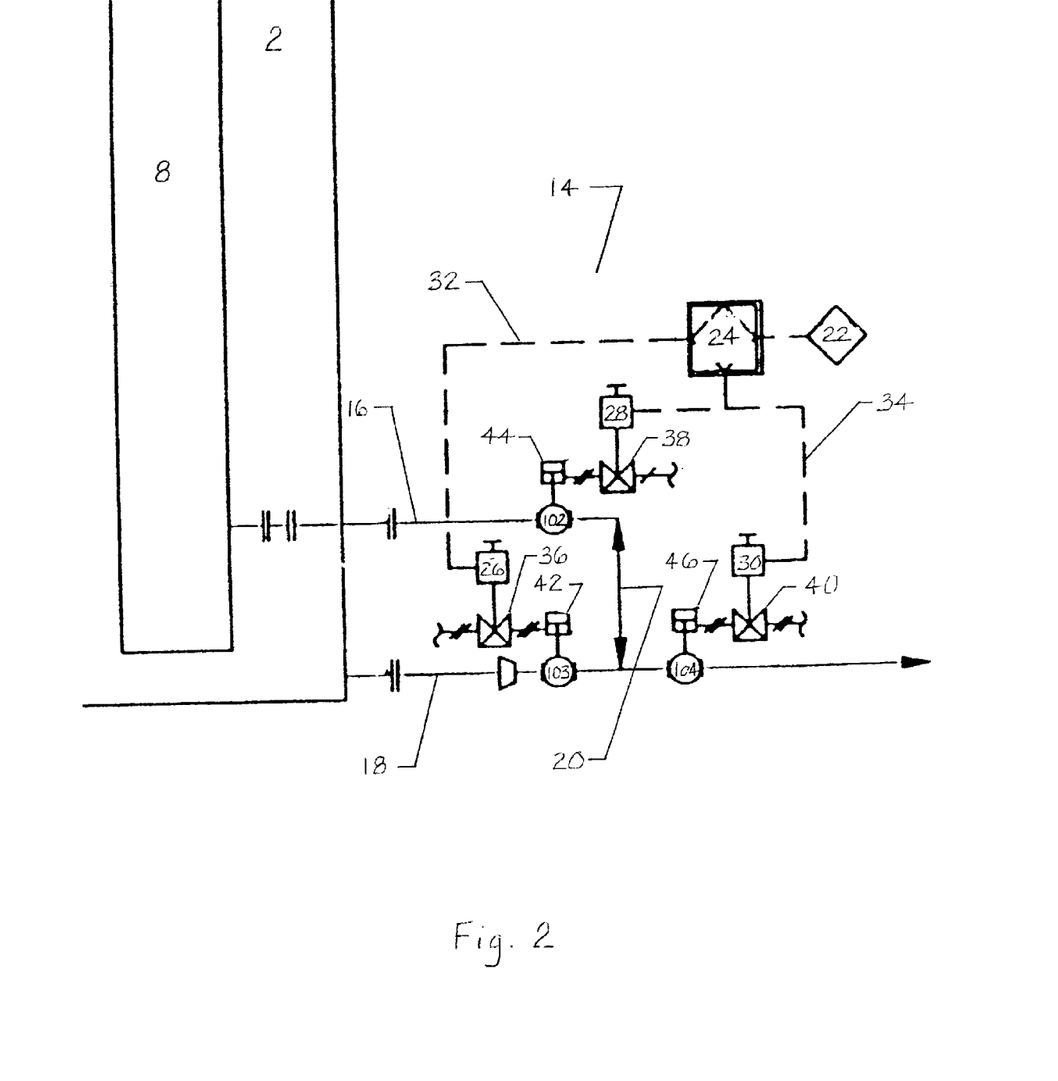
FIG. 2 is a schematic view of a portion of the biological reactor illustrated in FIG. 1.

The chamber 2 and the vessel 8 are connected for fluid flow communication through a valve and pipe assembly 14, as illustrated in FIG. 2, the significance of which fluid flow communication will become apparent subsequently during the discussion of the method according to this invention.

The valve and pipe assembly 14 consists of three valves (102, 103, and 104) and three lengths of pipe (16, 18, and 20), as shown in FIG. 2. A vessel pipe 16 is positioned at the bottom of the vessel 8, a chamber pipe 18 is positioned at the bottom of the chamber 2, and a connecting pipe 20 connects the vessel pipe 16 and the chamber pipe 18. The vessel pipe 16 contains one two-way directional valve 102, and the chamber pipe 18 contains two two-way directional valves 103 and 104.

Another embodiment of a system according to this invention includes automatic operation of the valve and pipe assembly 14. Operator controlled instruments 22 and 24 energize solenoids 26, 28, and 30, through electrical connections 32 and 34. The solenoids 26, 28, and 30, deliver power to instrument air supplies 36, 38, and 40 respectively. The instrument air supplies 36, 38, and 40 feed air to actuators 42, 44, and 46 respectively. The actuators 42, 44, and 46 ultimately shift the two-way directional valves 103, 102, and 104 respectively, in their desired positions based on signals received from operator input at the control instruments 22 and 24. The solenoids 26, 28, and 30 may be overridden to permit manual operation of the valves 102, 103, and 104, which is the preferred mode of operation.

Figure 3:
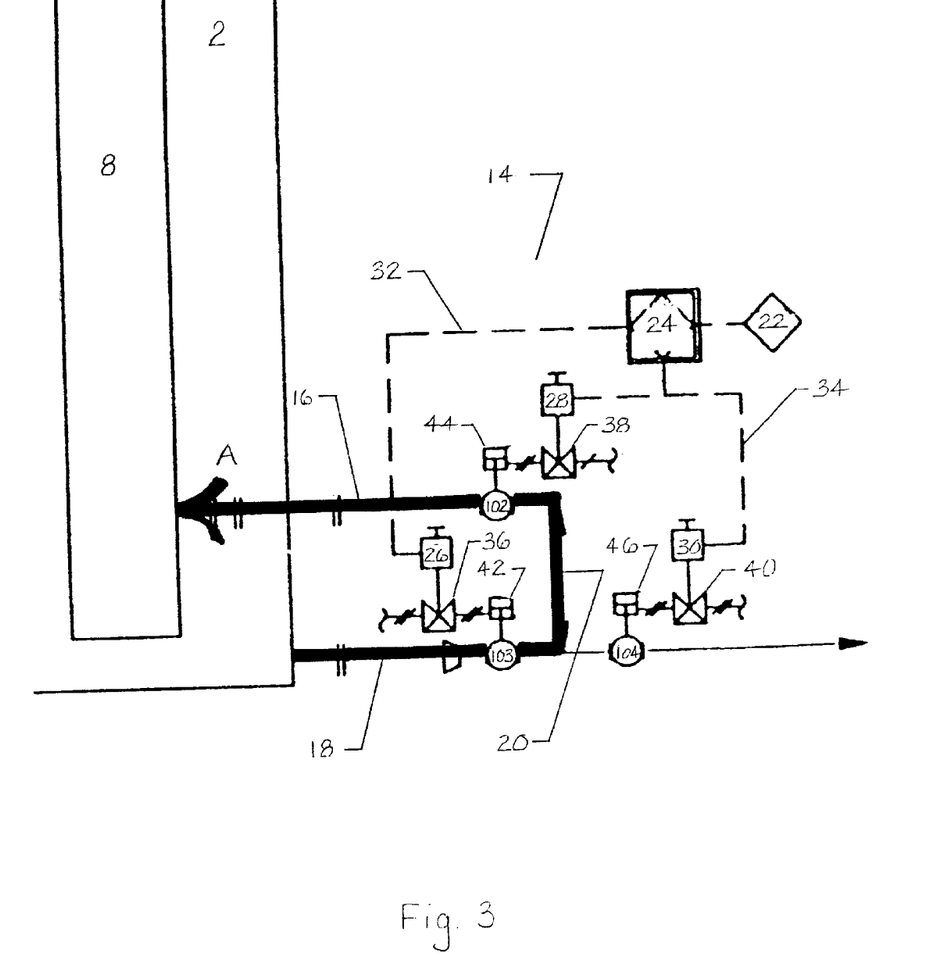
FIG. 3 is a schematic view of the portion of the biological reactor illustrated in FIG. 2, illustrating a flow path "A."

Referring to FIG. 3, the system according to this invention is configured such that when the vessel 8 is empty, valve 104 is in its closed position, and valves 102 and 103 are opened, gravity urges influent 4 and biomass 6 from the chamber 2 to the vessel 8 to be stored. The flow of influent 4 and biomass 6 extends along the path labeled "A" in FIG. 3. More specifically, influent 4 and biomass 6 flow from the chamber 2, through the chamber pipe 18, through the connecting pipe 20, through the vessel pipe 16, and into the vessel 8 along path "A."

Figure 4:
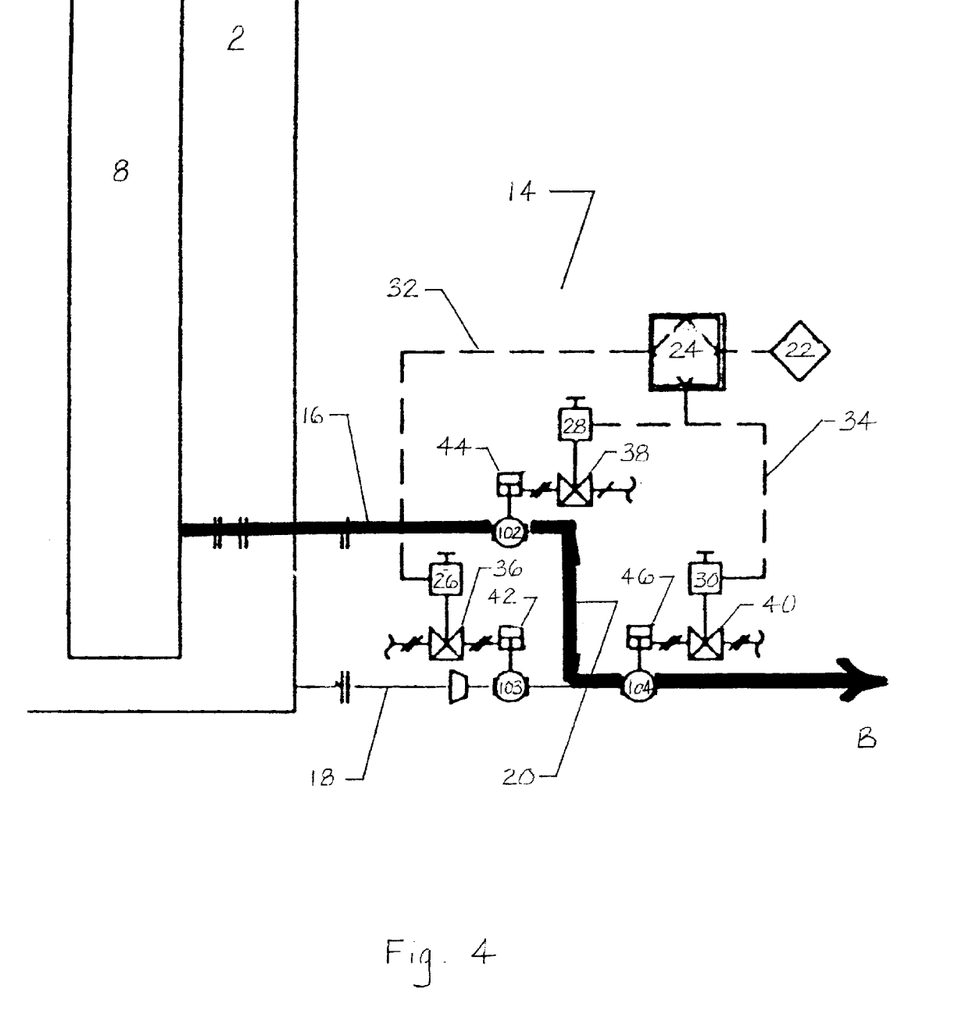
FIG. 4 is a schematic view of the portion of the biological reactor illustrated in FIG. 2, illustrating a flow path "B."

Referring to FIG. 4, when valve 103 is in its closed position and valves 102 and 104 are opened, the stored influent 4 and biomass 6 are drained from the vessel 8. The flow of influent 4 and biomass 6 extends along the path labeled "B" in FIG. 4. More specifically, influent 4 and biomass 6 flow from the vessel 8, through the vessel pipe 16, through the connecting pipe 20, and through the chamber pipe 18 to a drain along path "B." Referring to FIG. 5, when valve 102 is in its closed position and valves 103 and 104 are opened, influent 4 and biomass 6 are drained from the chamber 2. The flow of influent 4 and biomass 6 extends along the path labeled "C" in FIG. 5. More specifically, influent 4 and biomass 6 flow from the chamber 2 through the chamber pipe 18 to a drain along path "C."

Figure 6:
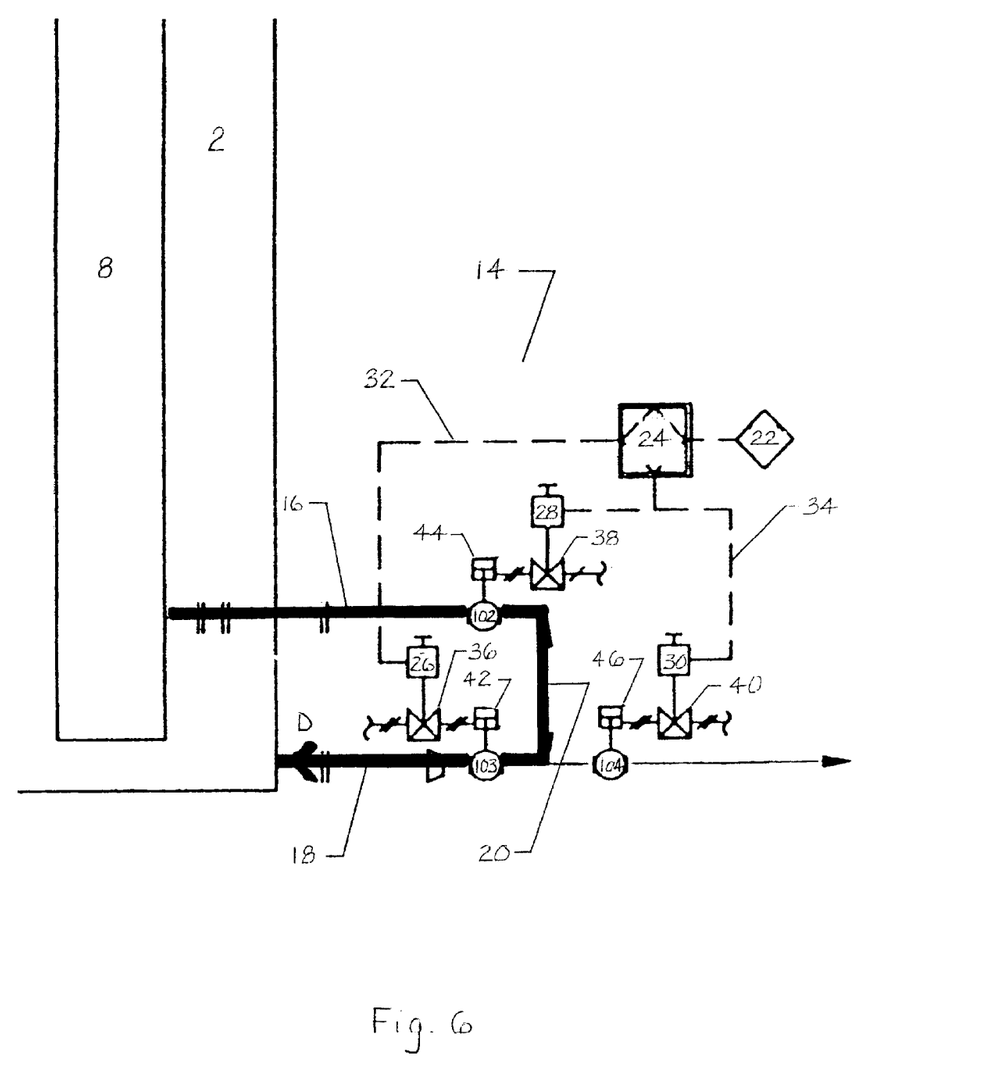
FIG. 6 is a schematic view of the portion of the biological reactor illustrated in FIG. 2, illustrating a flow path "D."

Referring to FIG. 6, when the chamber 2 is substantially empty, valve 104 is in its closed position, and valves 102 and 103 are opened, gravity urges the stored influent 4 and biomass 6 from the vessel 8 to the chamber 2. The flow of influent 4 and biomass 6 extends along the path labeled "D" in FIG. 6. More specifically, influent 4 and biomass 6 flow from the vessel 8, through the vessel pipe 16, through the connecting pipe 20, through the chamber pipe 18, and into the chamber 2 along path "D."

The preferred material for use in forming the vessel 8 is polyvinyl chloride. However, coated carbon steel is suitable as well. The materials selected may vary within the scope of this invention, as long as the selected material sufficiently insulates the stored biomass 6 and does not react with the influent 4 or biomass 6.

One embodiment of a method according to this invention begins with a biological reactor operator confirming the biomass 6 in the chamber 2 is robust. Optionally, periodic or continuous aeration of the influent 4 and biomass 6 in the chamber 2 can be performed to help to maintain the viability of the biomass 6. Such aeration can be conducted in any known manner, and piping is optionally provided to introduce aeration gas into the interior region of the vessel 8.

After confirming the biomass 6 in the chamber 2 is robust, the operator then manually opens valves 102 and 103 so that gravity urges influent 4 and biomass 6 from the chamber 2 to the empty vessel 8, as shown in FIG. 3. Valves 102 and 103 are then manually shut, and the newly received influent 4 and biomass 6 are stored in the vessel 8 for a predetermined time. At the end of the predetermined time, valves 102 and 104 are manually opened, and the stored influent 4 and biomass 6 are drained from the vessel 8, as shown in FIG. 4. The operator again confirms that the biomass 6 in the chamber 2 is robust, and the process is repeated.

This continuous or periodic transfer of robust biomass 6 from the chamber 2 to the vessel 8 ensures there is always a quantity of robust biomass 6 stored in the vessel 8, readily available to inoculate if a loss of biomass activity is detected in the chamber 2. In one exemplary embodiment of the invention, the frequency of this continuous or periodic transfer can range from as short as about 30 minutes or less to as long as about 30 days or more.

Figure 5:
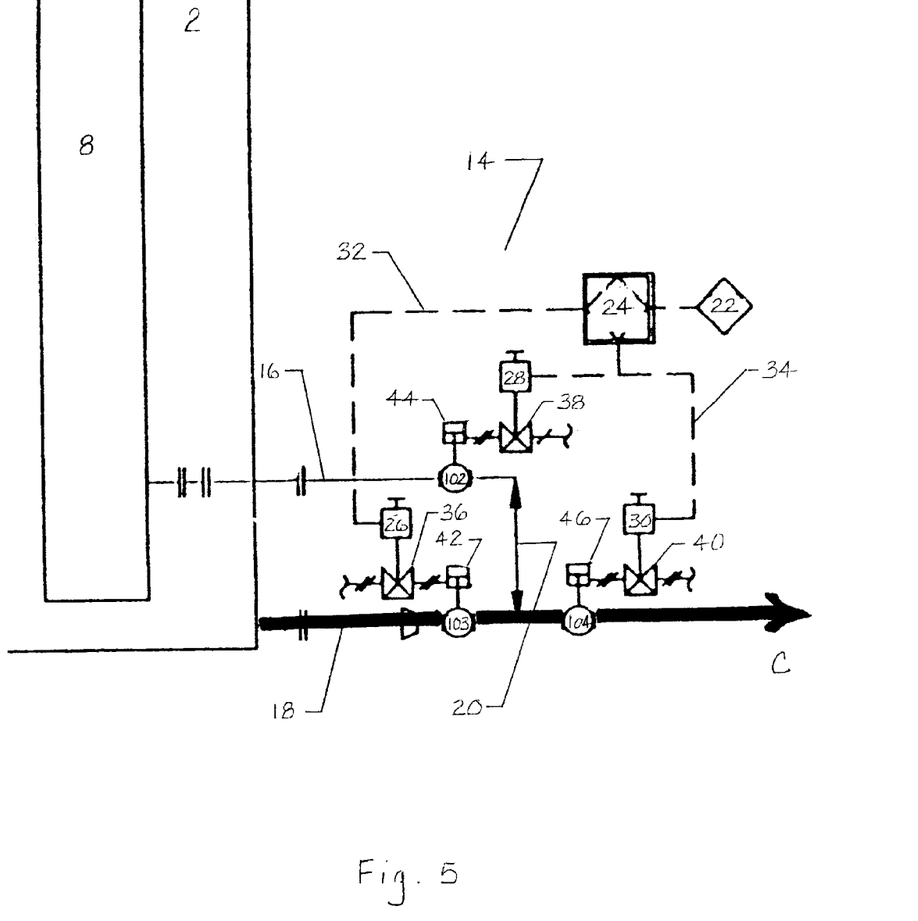
FIG. 5 is a schematic view of the portion of the biological reactor illustrated in FIG. 2, illustrating a flow path "C."

The above-described embodiment of a method according to this invention is continually repeated, until a loss of biomass 6 activity is detected in the chamber 2. When this occurs, the influent 4 and biomass 6 in the chamber 2 are tainted or may be "killed." However, the influent 4 and biomass 6 stored in the vessel 8 are isolated from the taint, and therefore the stored biomass 6 remains robust. The operator drains the tainted influent 4 and biomass 6 from the chamber 2 by opening valves 103 and 104, as illustrated in FIG. 5. Valve 104 is then shut, and the operator opens valve 102 so that gravity urges the stored influent 4 and biomass 6 from the vessel 8 to the empty chamber 2, as shown in FIG. 6. The operator then shuts valves 102 and 103 and replenishes the chamber 2 with new influent 4. The biological reactor is once again operational, and the above-described embodiment of a method according to this invention continues.

All of this takes place on-site through the operation of the valve assembly 14, illustrated in FIG. 2, and avoids the significant time delays and costs associated with lab-developed inoculum.

Another embodiment of a method according to this invention involves a biological reactor that consists of a chamber 2 without a built-in vessel 8. A vessel 8 can be retrofitted inside a chamber 2 with the associated valve and pipe assembly 14 installed as described previously and illustrated in FIG. 2.

In the above-described exemplary embodiment of a system according to this invention, the volume of the vessel 8 is less than or equal to about 50 percent of that of the chamber 2. For example, and solely for the purpose of illustration, if the vessel 8 has an inner diameter of 22 inches, and a height of 32 feet for a volume of 628 gallons, the chamber 2 may have an inner diameter of 30 feet and a height of 33 feet for a volume of 174,490 gallons. Sizing of the system is based on system requirements.

The above-described embodiments of a system and method according to this invention provide an improved system and method over conventional methods for renewing biological activity in a biological reactor. The system and method of the present invention avoid many significant costs and time delays of conventional methods of inoculation in biological reactors. For example, conventional methods may consist of fermenting and thickening the inoculum in a laboratory to suit a particular application, which often takes several weeks. During the time elapsed until the inoculum is prepared, the biological reactor is not operational. This period of downtime can be costly and highly inefficient. Conversely, the present invention ensures there is always a quantity of robust biomass 6 stored in the vessel 8, readily available to inoculate the biological reactor if a loss of biomass activity is detected in the chamber 2.

An additional contributor to the cost and time delays of conventional methods is that after the inoculum is prepared, it must be transported from the laboratory to the biological reactor. Because the laboratory in which the inoculum is prepared is often remote from the biological reactor, the cost for such transportation is usually significant. Once again, these factors are overcome by the present invention since the quantity of robust biomass 6 is stored in the vessel 8, on-site, and is readily available to inoculate if a loss of biomass activity is detected in the chamber 2.

Finally with respect to conventional methods, once shipped or otherwise transported to the field location, the lab-developed inoculum may then need time to acclimate to actual field conditions. While efforts are typically made to simulate the conditions of the biological reactor at the laboratory, the inoculum will often need time to adjust to the actual biological reactor and the conditions under which it operates. This acclimation period also extends the downtime or recovery time of the biological reactor. Acclimation is not an issue, however, with the present invention, since the quantity of robust biomass 6 is already stored at or proximal to the actual biological reactor, and therefore at or near the conditions under which it operates.

Overall, the present invention avoids the costs associated with producing lab-developed inoculum for each application, combined with the field labor necessary to handle the shipment and introduce the inoculum to the biological reactor.

Although exemplary embodiments of the system and method according to this invention have been described, there are others that support the spirit of the invention and are therefore within the contemplated scope of the invention. For example, with respect to the configuration of the chamber 2 or the vessel 8, the chamber 2 and/or vessel 8 may include a material concentration device to concentrate material within the chamber 2 or vessel 8. Such a material concentration device is optionally used to augment the potency of the influent 4 and biomass 6 within the chamber 2 or vessel 8. In one exemplary embodiment, a material concentration device is combined with the vessel 8 to concentrate material within the vessel 8. In such embodiment, the concentration device is optionally part of the vessel 8 or can be positioned externally of the vessel 8. Such a material concentration device, which may be located inside or outside the chamber 2 or vessel 8, can be a filter, strainer, screen, separator, purifier, or any other structure that provides for or facilitates material concentration.

The location of the vessel 8 is not limited to inside the chamber 2, as is illustrated in FIG. 1. The vessel 8 may be located outside the chamber 2, as long as the open top 12 of the vessel 8 extends above the level of the influent 4 and biomass 6 contained in the chamber 2, and suitable conditions such as temperature are maintained.

The method according to this invention is not limited to a biological reactor operator confirming the biomass 6 in the chamber 2 is robust before proceeding with the transfer of influent 4 and biomass 6 from the chamber 2 to the empty vessel 8. Certain situations may occur where the operator will optionally initiate a "blind" transfer (transferring influent 4 and biomass 6 from the chamber 2 to the empty vessel 8 without confirming that the biomass 6 in the chamber 2 is robust or acceptable).

The means for moving the influent 4 and biomass 6 throughout the biological reactor system is not limited to gravity. Fluid movement may be achieved via a pump. The valves 102, 103, and 104, are not limited to manual operation. The valves may be automatically operated, whereby the biological reactor operator pushes appropriate buttons to configure the valves to achieve the desired flow paths. Alternatively, the entire valve assembly may be computer controlled, whereby a computer operates the valves automatically based on predetermined specified times, as described previously and illustrated in FIG. 2. Furthermore, the valve assembly may be remotely operated via on-line computer controlled instrumentation. Accordingly, the transfer of material from the vessel to the chamber can be accomplished (a) by manual manipulation of a flow control apparatus by an operator of the system, (b) automatically based on a predetermined or varying time interval, (c) by on line instrumentation or otherwise configured instrumentation that detects conditions within the system or actuates transfer on one or more other bases, or (d) some combination of all or some of the foregoing transfer methods.

The vessel 8 is only one of many possible embodiments of a means for substantially isolating influent and biomass received from the chamber. The isolating means can also be a compartment, a wall, a partition, a tank, or any other structure that provides at least a partial barrier between a portion of influent and biomass and the remaining influent and biomass.

Similarly, the valve and pipe assembly 14 is only one of many possible embodiments of a means for delivering isolated influent and biomass to the chamber. The delivery means can also be an opening, a passageway, a pump, a channel, a valve, or any other structure through or along which isolated influent and biomass can flow to the interior of the chamber. Such delivering means can operate by power (e.g., a pump) or by gravity (e.g., height differential).

It will be appreciated that other modifications can be made to the illustrated embodiments without departing from the scope of the invention. The scope of the invention is separately defined in the appended claims.

What is claimed is:

1. A system for inoculating a biological chamber configured to contain influent and biomass to degrade contaminants in the influent, said system comprising:

a vessel configured to receive influent and biomass from the chamber and to substantially isolate the received influent and biomass from that contained in the chamber;

said vessel also being configured to deliver the isolated influent and biomass to the chamber, thereby facilitating inoculation of the chamber, wherein at least a portion of said vessel is positioned within the chamber.

2. The system recited in claim 1, wherein the capacity of said vessel is less than that of the chamber.

3. The system recited in claim 2, wherein the capacity of said vessel is less than or equal to about 50% of that of the chamber.

4. The system recited in claim 1, further comprising a valve assembly coupled to selectively permit the flow of influent and biomass between said vessel and the chamber.

5. The system recited in claim 4, wherein said valve assembly is configured for manual operation.

6. The system recited in claim 4, wherein said valve assembly is configured for automatic operation.

7. The system recited in claim 1, further comprising a pump to urge influent and biomass from said vessel to the interior of the chamber.

8. The system recited in claim 1, said system being configured to transport influent and biomass between said vessel and said chamber by gravity forces.

9. The system recited in claim 1, wherein said vessel is substantially cylindrical in shape.

10. The system recited in claim 1, wherein a top portion of said vessel extends above the level of the influent and biomass in the chamber.

11. The system recited in claim 1, wherein said vessel defines an open top.

12. The system recited in claim 1, said vessel further comprising an influent and biomass drain.

13. The system recited in claim 1, further comprising an influent and biomass drain connected to the chamber.

14. The system recited in claim 1, said system being adapted to maintain the isolated influent and biomass at substantially the same temperature as in the chamber.

15. A system for inoculating a biological chamber configured to contain influent and biomass to degrade contaminants in the influent, said system comprising:

means for substantially isolating influent and biomass received from the chamber from influent and biomass contained in the chamber; and means for delivering isolated influent and biomass to the chamber, thereby facilitating inoculation of the chamber, wherein at least a portion of said isolating means is positioned within the chamber.

16. The system recited in claim 15, further comprising means for controlling the flow of isolated influent and biomass to the chamber.

17. The system recited in claim 15, further comprising means for urging isolated influent and biomass to the chamber.

18. The system recited in claim 15, said system being adapted to maintain isolated influent and biomass at substantially the same temperature as in the chamber.

19. A method for inoculating a biological reactor having a chamber adapted to contain influent and biomass to degrade contaminants in the influent, said method comprising the steps of:

(a) substantially isolating in a vessel, a portion of influent and biomass received from the chamber from influent and biomass in the chamber; and (b) delivering at least a portion of the isolated influent and biomass to the chamber, thereby inoculating the chamber, wherein at least a portion of the vessel is positioned within the chamber.

20. The method recited in claim 19, further comprising the step of maintaining the isolated influent and biomass in the vessel at substantially the same temperature as in the chamber.

21. The method recited in claim 19, further comprising the step of detecting a reduction in biological activity in the chamber.

22. The method recited in claim 19, further comprising the step of isolating in the vessel another portion of influent and biomass received from the chamber, thereby replenishing isolated influent and biomass delivered to the chamber.

23. The method recited in claim 19, wherein said isolating step is performed periodically.

24. The method recited in claim 19, further comprising discharging isolated influent and biomass from the vessel.

25. The method recited in claim 19, further comprising maintaining isolated influent and biomass in the vessel under substantially the same conditions as in the chamber.

26. The method recited in claim 19, further comprising discharging at least a portion of influent and biomass from the chamber before said delivering step.

27. The method recited in claim 19, further comprising substantially emptying the chamber and re-introducing influent and biomass into the chamber before said delivering step.

28. A method for configuring a biological reactor for inoculation, wherein the biological reactor includes a chamber adapted to contain influent and biomass to degrade contaminants in the influent, said method comprising the steps of:

(a) configuring a vessel to receive influent and biomass from the chamber;

(b) configuring the vessel to substantially isolate received influent and biomass from that in the chamber; and (c) configuring the vessel to return at least a portion of the isolated influent and biomass to the chamber, wherein at least a portion of the vessel is positioned within the chamber.

29. The method recited in claim 28, further comprising configuring the vessel to maintain isolated influent and biomass under substantially the same conditions as in the chamber.

30. A biological reactor comprising:

a chamber configured to contain influent and biomass to degrade contaminants in the influent;

a vessel configured to substantially isolate influent and biomass from that contained in said chamber, said vessel being configured to receive influent and biomass from said chamber, and said vessel also being configured to deliver isolated influent and biomass to said chamber, wherein at least a portion of said vessel is positioned within said chamber, thereby facilitating inoculation of the biological reactor.

31. The biological reactor recited in claim 30, wherein said vessel comprises an inlet positioned to receive influent and biomass from said chamber.

32. The biological reactor recited in claim 31, wherein said inlet is formed by a port in said vessel.

33. The biological reactor recited in claim 30, wherein said vessel comprises an outlet positioned to deliver isolated influent and biomass to said chamber.

34. The biological reactor recited in claim 33, wherein said outlet is formed by a port in said vessel.

35. A method for providing inoculum for a biological reactor having a chamber adapted to contain influent and biomass to degrade contaminants in the influent, said method comprising the steps of:

(a) substantially isolating a portion of influent and biomass within the chamber from remaining influent and biomass in the chamber; and (b) maintaining the isolated influent and biomass at substantially the same temperature as the remaining influent and biomass in the chamber.

36. The method recited in claim 35, further comprising discharging isolated influent and biomass.

37. The method recited in claim 36, further comprising isolating an additional portion of influent and biomass, thereby replenishing discharged influent and biomass.

38. The method recited in claim 35, said isolating step comprising delivering influent and biomass from the chamber into a vessel.

39. The method recited in claim 38, said maintaining step comprising maintaining the vessel at least partially within the chamber.

* * * * *